(12) United States Patent
Rock et al.

(10) Patent No.: US 6,407,267 B1
(45) Date of Patent: Jun. 18, 2002

(54) METHOD FOR THE PREPARATION OF CITALOPRAM

(75) Inventors: Michael Harold Rock, Hvidovre; Hans Petersen, Vanløse; Peter Ellegaard, Jystrup, all of (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/891,874

(22) Filed: Jun. 25, 2001

Related U.S. Application Data

(63) Continuation of application No. PCT/DK99/00581, filed on Oct. 25, 1999.

(51) Int. Cl.$^7$ ................... C07D 307/87; C07C 255/50
(52) U.S. Cl. ................... 549/467; 558/44; 558/58; 558/415
(58) Field of Search ................... 558/44, 58, 415; 549/467

(56) References Cited

U.S. PATENT DOCUMENTS

| | | | |
|---|---|---|---|
| 3,467,675 A | 9/1969 | Petersen et al. | 260/346.2 |
| 4,136,193 A | 1/1979 | Bogeso et al. | 424/285 |
| 4,650,884 A | 3/1987 | Bogeso | 549/467 |
| 4,943,590 A | 7/1990 | Boegesoe et al. | 514/469 |
| 5,296,507 A | 3/1994 | Tanaka et al. | 514/465 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |

FOREIGN PATENT DOCUMENTS

| | | | |
|---|---|---|---|
| EP | 1 095 926 | 5/2001 | C07C/33/46 |
| WO | 98/19511 | 5/1998 | |
| WO | 98/19512 | 5/1998 | |
| WO | 98/19513 | 5/1998 | |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | C07D/307/87 |
| WO | 00/39112 | 7/2000 | C07D/307/87 |
| WO | 00/44738 | 8/2000 | C07D/307/88 |
| WO | 01/45483 | 6/2001 | |
| WO | 01/47877 | 7/2001 | |
| WO | 01/665536 | 9/2001 | C07D/307/87 |

OTHER PUBLICATIONS

U.S. Patent application Ser. No. 09/794,762, filed Feb. 26, 2001.
U.S. Patent application Ser. No. 09/794,755, Feb. 26, 2001.
U.S. Patent application Ser. No. 09/830,109, filed Oct. 19, 1999 (International filing date).
U.S. Patent application Ser. No. 09/888,067, filed Jun. 22, 2001.
U.S. Patent application Ser. No. 09/917,180, filed Jul. 27, 2001.
U.S. Patent application Ser. No. 09/692,653, filed Oct. 19, 2000.
U.S. Patent application Ser. No. 09/930,110, filed Aug. 14, 2001.
U.S. Patent application Ser. No. 09/977,920, filed Oct. 15, 2001.
U.S. Patent application Ser. No. 10/012,025, filed Nov. 6, 2001.
U.S. Patent application Ser. No. 10/012,054, filed Nov. 6, 2001.
U.S. Patent application Ser. No. 10/035,005, filed Dec. 20, 2001.
U.S. Patent application Ser. No. 10/046,126, filed Jan. 8, 2002.
Levy, L.F., "4–Aminophthalide and Some Derivatives", *J. Chem. Soc.* pp. 867–870 (1931).
Tirouflet J., "Phtalide Substitutes en 5", *Bull. Soc. Sci. de Bretagne* 26:35–43 (1951).
Bigler, Allan et al., "Quantitative Structure–activity Relationships in a Series of Selective 5–HT uptake inhibitors, " *Eur. J. Med. Chem.* 3:289–295 (1997).
Forney L., "Reaction of Terephthalic Acid with Formaldehyde in Sulfur Trioxide Media," *J. Org. Chem.* 35:1695–1696 (1970).
Dordor et al., "Reaction of Oxazolines with Phosphorus Oxychloride," *Tetrahedron Letters* 24:1437–1440 (1983).
Barton et al., *Comprehensive Organic Chemistry. The Synthesis and Reactions of Organic Compounds*, vol. 2, pp. 1024–1025.

Primary Examiner—Bernard Dentz
(74) *Attorney, Agent, or Firm*—Darby & Darby

(57) ABSTRACT

A method for the preparation of citalopram comprising reaction of a compound of Formula (IV),

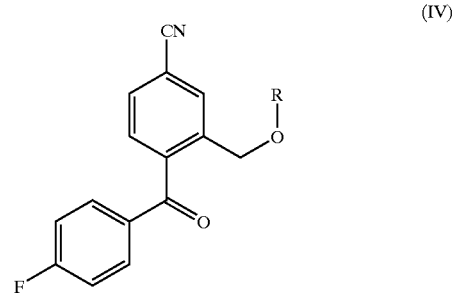

wherein R is $C_{1-6}$ alkyl, acyl, $C_{1-6}$ alkylsulfonyl or arylsulfonyl, with 3-(N,N-dimethylamino)-propyl magnesium halide, to prepare citalopram.

17 Claims, No Drawings

METHOD FOR THE PREPARATION OF CITALOPRAM

This is a continuation of international application Ser. No. PCT/DK99/00581, filed Oct. 25, 1999, the entire disclosure of which is hereby incorporated by reference.

The present invention relates to a method for the preparation of the well known anti-depressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well known antidepressant drug that has now been on the market for some years and has the following structure:

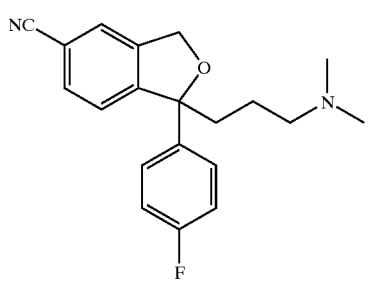

Formula I

It is a selective, centrally acting serotonin (5-hydroxytryptamine; 5-HT) reuptake inhibitor, accordingly having antidepressant activities. The antidepressant activity of the compound has been reported in several publications, eg. J. Hyttel, *Prog. Neuro-Psychopharmacol. & Biol. Psychiat.*, 1982, 6, 277–295 and A. Gravem, *Acta Psychiatr. Scand.*, 1987, 75, 478–486. The compound has further been disclosed to show effects in the treatment of dementia and cerebrovascular disorders, EP-A 474580.

Citalopram was first disclosed in DE 2,657,271, corresponding to U.S. Pat. No. 4,136,193. This patent publication describes the preparation of citalopram by one method and outlines a further method which may be used for preparing citalopram.

According to the process described, the corresponding 1-(4-fluorophenyl)-1, 3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide. According to the method, which is only outlined in general terms, citalopram may be obtained by ring closure of the compound:

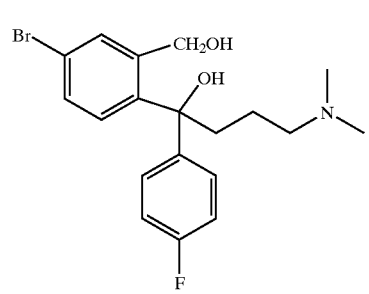

Formula II in the presence of a dehydrating agent and subsequent exchange of the 5-bromo group with cuprous cyanide. The starting material of Formula 11 is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884 according to which an intermediate of the formula

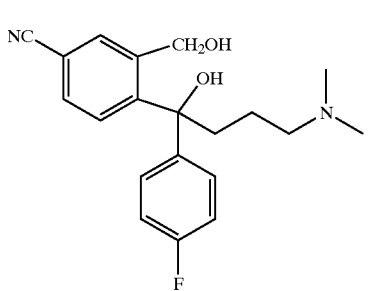

Formula III is subjected to a ring closure reaction by dehydration with strong sulfuric acid in order to obtain citalopram. The intermediate of Formula III was prepared from 5-cyanophthalide by two successive Grignard reactions, i.e. with 4-fluorophenyl magnesium halogenide and N,N-dimethylaminopropyl magnesium halogenide, respectively.

Further processes are disclosed in International patent application Nos. WO 98019511, WO 98019512 and WO 98019513. WO 98019512 and WO 98019513 relate to methods wherein a 5-amino-, 5-carboxy- or 5-(sec. aminocarbonyl)phthalide is subjected to two successive Grignard reactions, ring closure and conversion of the resulting 1,3-dihydroisobenzofuran derivative to the corresponding 5-cyano compound, i.e. citalopram. International patent application No. WO 98019511 discloses a process for the manufacture of citalopram wherein a (4-substituted-2-hydroxymethylphenyl-(4-fluorophenyl)methanol compound is subjected to ring closure and the resulting 5-substituted 1-(4-fluorophenyl)-1,3-dihydroisobenzofuran converted to the corresponding 5-cyano derivative which is alkylated with a (3-dimethylamino)propylhalogenide in order to obtain citalopram.

Finally, methods of preparing the individual enantiomers of citalopram are disclosed in U.S. Pat. No. 4,943,590 from which it also appears that the ring closure of the intermediate of Formula III may be carried out via a labile ester with a base.

It has now, surprisingly, been found that citalopram may be manufactured by a novel favourable and safe procedure using convenient starting materials.

SUMMARY OF THE INVENTION

Accordingly, the present invention relates to a novel method for the preparation of citalopram comprising reaction of a compound of Formula IV

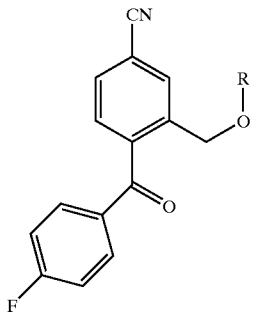

wherein R is $C_{1-6}$ alkyl, acyl, $C_{1-6}$ alkylsulfonyl or arylsulfonyl, with 3-(N, N-dimethylamino)-propyl magnesium halide, preferably of 3-(N,N-dimethylamino)propyl magnesium chloride to afford citalopram Formula I

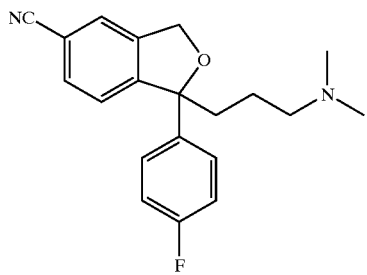

which is isolated as the base or a pharmaceutically acceptable salt thereof.

In another aspect, the present invention provides the novel intermediates of Formula IV.

In a further aspect, the invention relates to methods for preparing the intermediates of Formula IV.

In yet another aspect of the invention, the compounds of Formula IV are used for the preparation of the racemic compound of Formula III.

Formula III

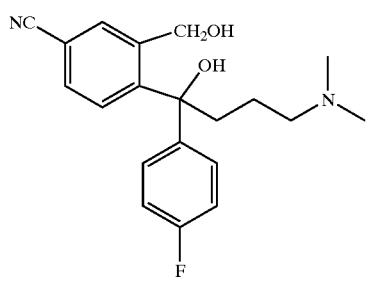

In yet another aspect, the present invention relates to an antidepressant pharmaceutical composition comprising citalopram manufactured by the process of the invention.

By the process of the invention, citalopram is obtained by a single step Grignard reaction from the compounds of Formula IV, wherein R is $C_{1-6}$ alkyl, acyl, $C_{1-6}$ alkylsulfonyl or arylsulfonyl

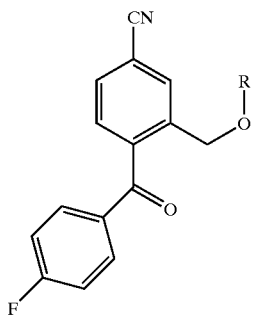

Surprisingly, the product of the Grignard reaction ring closes spontaneously and directly to citalopram, and accordingly the reaction of compound of Formula IV with the Grignard reagent leads to citalopram in one step.

Furthermore, according to the invention the compounds of Formula IV may be prepared by three different methods.

One of these methods includes protection of the hydroxymethylalcohol of (4-cyano-2-hydroxymethylphenyl)(4-fluorophenyl)methanol of Formula VI:

followed by an oxidation to afford the compounds of Formula IV, wherein R is $C_{1-6}$ alkyl, acyl, $C_{1-6}$ alkylsulfonyl or arylsulfonyl.

The oxidation of the compounds of Formula V, may be performed by any convenient oxidation agent, preferably performed by $Na_2WO_4$.

The starting material of the compound of Formula VI may be prepared as described in International Patent Application No. PCT/DK97/00511.

Another method for preparing the compounds of Formula IV includes the reaction of 5-cyanophthalide with 4-fluorophenylmagnesiumhalide, preferably 4-fluorophenyl-magnesiumbromide followed by the reaction with R-X, wherein R is as defined above and X is a leaving group, preferably R-X is pivaloylchloride, 3,5-dimethoxybenzoylchloride, methyliodide, ethylbromide, tosyichloride, Me$_2$SO$_4$ or MeSO$_2$Cl.

The reaction is illustrated below:

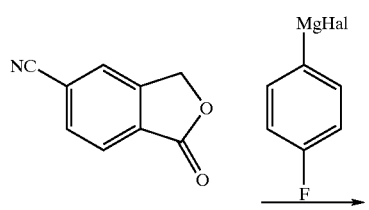

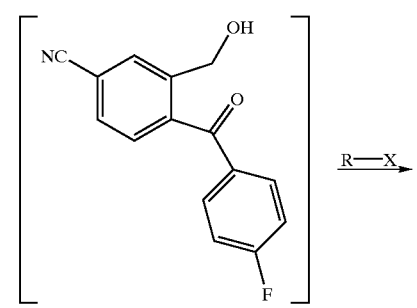

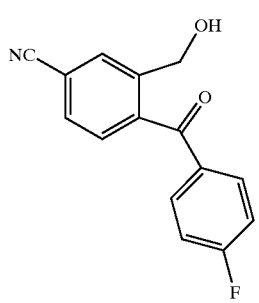

The starting material, 5-cyanophthalide, may be prepared as described in Tirouflet, J.; Bull.Soc.Sci. Bretagne 26, 1959,35.

According to the third method for preparing the compound of Formula IV, one of the enantiomers of the compound of Formula III, i.e. the R-enantiomer, is subjected to protection and dehydration to give the compound of Formula VII, which is oxidised to give the ketone of Formula IV.

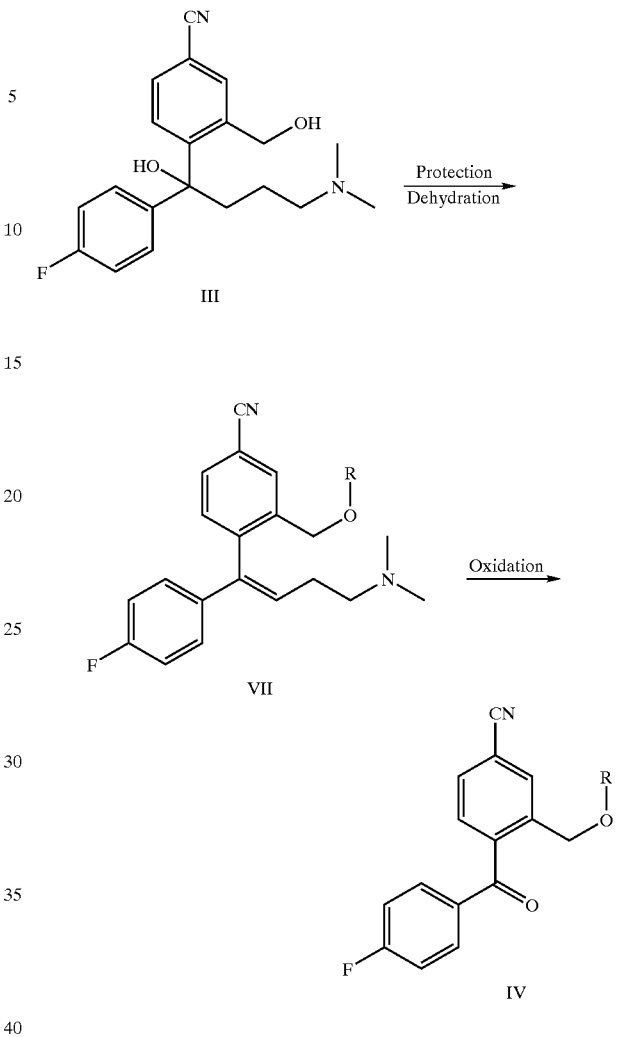

In this way, the R-enantiomer of Formula III may be used in the preparation of racemic citalopram.

The oxidative cleavage of the compound of Formula VII is effected by oxidation, preferably performed by MnO$_4^-$ (permanganates), or ozone, RuCl$_3$, OsO$_4$.

Citalopram is on the market as an antidepressant drug in the form of the racemate. However, in the near future the active S-enantiomer of citalopram is also going to be introduced to the market.

The active S-enantiomer of citalopram may be prepared from the compound of Formula III by separation of the S-enantiomer and the R-enantiomer followed by ring closure of the S-enantiomer as described in U.S. Pat. No. 4,943,590. The R-enantiomer of the compound of Formula III has previously not been used after separation.

Furthermore, according to a further aspect of the invention, after conversion of the R-enantiomer of Formula III to the non-optically active compound of Formula IV, the racemic compound of Formula III may be prepared as illustrated below:

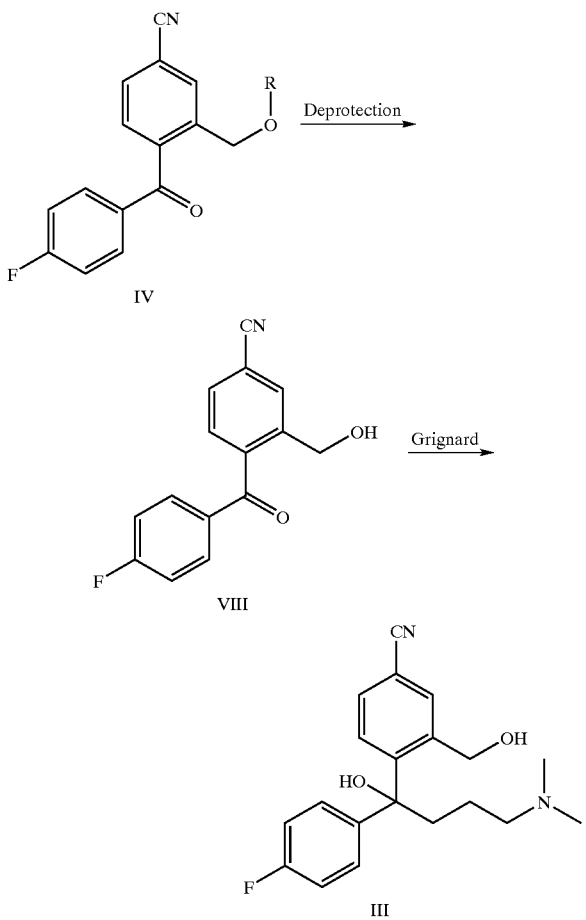

The racemic compound of Formula III may be separated into the optically active enantiomers by the procedure described in U.S. Pat. No. 4,943,590 thereby obtaining the S-enantiomer of the compound of Formula III, which is used in the preparation of S-citalopram. The R-enantiomer of the compound of Formula III can be recycled once more in the process cycle described above.

In this way, the R-enantiomer of Formula III may be converted to S-citalopram.

Other reaction conditions, solvents, etc. for the reactions described above are conventional conditions for such reactions and may easily be determined by a person skilled in the art.

Throughout the specification and claims, the term $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

The term aryl refers to a mono- or bicyclic carbocyclic aromatic group, such as phenyl and naphthyl, in particular phenyl or ring substituted phenyl.

The term heteroaryl refers to a mono- or bicyclic heterocyclic aromatic group, such as indolyl, thienyl, pyrimidyl, oxazolyl, isoxazolyl, thiazolyl, isothiazolyl, imidazolyl, benzofuranyl, benzothienyl, pyridyl, and furanyl, in particular pyrimidyl, indolyl, and thienyl.

Acyl is used in the meaning of $C_{1-6}$ alkyl- or aryl- or heteroarylcarbonyl wherein $C_{1-6}$ alkyl and aryl and heteroaryl are as defined above.

Halogen means chloro, bromo or iodo.

Preferably leaving group means halogenide or sulphonate.

In a preferred embodiment of the invention, R is acyl, preferably pivaloyl, acetyl or optionally substituted benzoyl.

The compound of general Formula I may be used as the free base or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-arninobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilisation of the solution and filling in suitable ampoules or vials. Any suitable additive conventionally used in the art may be added, such as tonicity agents, preservatives, antioxidants, etc.

EXAMPLES

The invention is further illustrated by the following examples.

Example 1

2,2-Dimethyl-propionic Acid 5-Cyano-2-[1-(4-fluoro-phenyl)-l-hydroxy-methyl]-benzyl Ester To a stirred solution of (4-cyano-2-hydroxymethylphenyl) (4-fluorophenyl)methanol (9.2 g, 0.037 mol) and triethylamine (4.0 g, 0.04 mol) was added pivaloyl chloride (4.2 g, 0.39 mol). After stirring for 60 minutes the reaction mixture was poured onto ice, extracted with diethyl ether (2×75 mL), dried (MgSO$_4$), and concentrated under reduced pressure to give a colourless oil (12.0 g). The compound was purified by chromatography (eluent hexane/ethyl acetate 1:9 to give the title compound (8.2 g, 70%).

$^1$H NMR (DMSO-D$_6$): 1.1 (s, 9H), 5.15 (m, 2H), 6 (bs, 1H), 6.25 (d, J=6 Hz, 1H), 7.1–7.2 (m, 2H, 7.3–7.4 (m, 2H), 7.7–7.9 (m, 3H).

Example 2

2,2-Dimethyl-propionic Acid 5-Cyano-2-[1-(4-fluoro-phenyl)-methanoyl]-benzyl Ester To a stirred solution of 2,2-dimethyl-propionic acid 5-cyano-2-[1-(4fluoro-phenyl)-1-hydroxy-methyl]-benzyl ester (8.0 g, 0.025 mol) in ethylacetate (20 mL) was added hydrogen peroxide solution 30% wt (10 g, 0.079 mol), Na$_2$WO$_4$.2H$_2$O (0.15 g, 0.0005 mol), and (n-Octyl) 3NCH$_3$.HSO$_4$ (0.23 g, 0.0005 mol). The mixture was then heated at reflux for 4 hrs, allowed to cool to room temperature and pored into dilute HCl, extracted with diethyl ether (2×50 mL), dried (MgSO$_4$) and concentrated under reduced pressure to give the title ketone compound (7.8 g, 97.5%).

Example 3

Acetic Acid 5-Cyano-2-[4-dimethylamino-1-(4-fluoro-phenyl)-but-1-enyl]-benzyl Ester, and the Oxalate Salt Thereof Method 3A. Acetic anhydride (103 g, 1 mol) was added dropwise to a stirred solution of 4-[4-dimethylamino-1-(4-fluoro-phenyl)-1-hydroxy-butyl ]-3-hydroxymethyl-benzonitrile (72 g, 0.21 mol) in acetonitrile (438 g) at 20° C. Once the addition was complete trimethylsilyl chloride (5.5 g, 0.05 mol) was added dropwise (resulting in an exothermic reaction temperature raised from 20 to 28° C.) and stirred overnight. Concentrated H$_2$SO$_4$ (14.5 g, 0.14 mol) was then added to the reaction mixture and the reaction mixture was then heated at 50° C. for 30 minutes (HPLC indicated completion of reaction). After cooling the reaction mixture was concentrated under reduced pressure and neutralized with aqueous ammonia solution (23%) and extracted with toluene (2 times). The organic phase was dried (MgSO$_4$) and concentrated under reduced pressure to give the title compound as a pale orange oil (69.5 g, 85%).

Characterised as the oxalate salt. A warm solution of oxalic acid (1. g, 0.0177 mol) in methanol (50 mL) was added to a stirred solution of the title alkene compound (6.63 g, 0.0173 mol) in methanol (50 mL). After allowing to cool, the crystals were isolated by filtration (7.4 g) and washed with cold methanol (10 mL). M.p. 168° C. $^1$H NMR (DMSO-D$_6$): 1.9 (s, 3H), 2.2 (m, 2H), 2.62 (s, 6H), 3.1 (t, J=6.2 Hz, 2H), 4.8 (s, 2H), 6.35 (t, J=7Hz, 1H) 7.1–7.25 (m, 4H), 7.42 (d, J=7 Hz, 1H), 7.9–8 (m, 2H).

$^{13}$C; NMR (DMSO-D6): 20.35, 24.98, 42.16, 55.54, 62.51, 111.17, 115.25, 115.59, 118.51, 124.85, 128.0, 128.18, 131.32, 132.43, 132.73, 135.65, 135.99, 138.68, 142.9, 164.72, 169.96. Anal. Calcd for C$_{24}$H$_{25}$N$_2$O$_6$F C, 63.14; H, 5.53; N, 6.14. Found, C, 63.1; H, 5.58; N, 6.12.

Acetic Acid 5-Cyano-2-[4-dimethylamino-1-(4-fluoro-phenyl)-but-1-enyl]-benzyl Ester Method 3B. Acetic anhydride (1112g, 10.8mol) was added dropwise to a stirred solution of 4-[4-Dimethylamino-1-(4-fluoro-phenyl)-1-hydroxy-butyl]-3-hydroxymethyl-benzonitrile (1000 g, 2.9 mol) in acetonitrile (1000 g) at 20° C. (resulting in an exothermic reaction temperature raised from 20 to 50° C.) and stirred for 2 hrs. Concentrated H$_2$SO$_4$ (300 g, 3 mol) was added to the reaction mixture, and the reaction mixture was then heated at 50° C. for 3 hrs (HPLC indicated completion of reaction). After cooling the reaction mixture was neutralized with aqueous ammonia solution (25%) and extracted with toluene (2 times). The organic phase was dried (MgSO$_4$) and concentrated under reduced pressure to give the title compound as a pale orange oil (1023 g, 92%).

Example 4

2,2-Dimethyl-propionic Acid 5-Cyano-2-[4-dimethylamino-1-(4-fluoro-phenyl)-but-1-enyl]-benzyl Ester, and the Oxalate Salt Thereof Method 4A. A solution of pivaloyl chloride (26.0 g, 0.215 mol) was added to a stirred solution of 4-[4-Dimethylamino-1-(4-fluoro-phenyl)-1-hydroxy-butyl]-3-hydroxymethyl-benzonitrile (72 g, 0.21 mol) and triethylamine (25.0 g, 0.247 mol) in acetonitrile (438 g) at 20° C. After 60 minutes, concentrated H$_2$SO$_4$ (40 mL) was added dropwise and the reaction mixture was heated at 70° C. for 180 min. The reaction mixture was allowed to cool to room temperature, neutralized with aqueous ammonia (25%) and extracted with diethylether. The organic phase was dried (MgSO$_4$) and concentrated under reduced pressure to give the title compound as a yellow oil (82 g, 96%). Characterized as the oxalate salt. (acetone) Mp 188° C. $^1$H NMR (DMSO-D$_6$): 1.07 (s, 9H), 2.2 (m, 2H), 2.6 (s, 6H), 3.05 (t, J=6.2 Hz, 2H), 4.725 (d, J=12 Hz, 1H), 4.85 (d, J=12 Hz, 1H), 6.3 (t, J=6.3 Hz, 1H) 7.1–7.3 (m, 4H), 7.42(d, J=7 Hz, 1H), 7.9–8 (m, 2H).

$^{13}$C; NMR (DMSO-D$_6$): 25.1, 26.71, 42.3; 55.67, 62.55, 111.21, 115.3, 115.64, 128.17, 131.33, 132.28, 136.13, 138.58, 142.76, 164.4 Anal. Calcd for C$_{27}$H$_{31}$N$_2$O$_6$F: C, 65.04; H, 6.28; N. 5.62. Found, C, 64.86; H, 6.63; N, 5.6.

2,2-Dimethyl-propionic Acid 5-Cyano-2-[4-dimethylamino-1-(4-fluoro-phenyl)-but-1-enyl]-benzyl Ester, and the Hydrogen Chloride Salt Method 4B. A solution of pivaloyl chloride (30.1 g, 0.25 mol) was added to a stirred solution of 4-[4-Dimethylamino-1-(4-fluoro-phenyl)-1-hydroxy-butyl)-3-hydroxymethyl-benzonitrile (85.5 g, 0.21 mol) in acetonitrile (290 mL) at 0° C. The reaction mixture was stirred for a further 60 minutes before concentrated H$_2$SO$_4$ (32.5 g, 0.33 mol) was added. Once the addition was complete, the reaction was heated at 70° C. for 180 minutes. The reaction mixture was allowed to cool to room temperature, and the acetonitrile (220 mL) was removed under reduced pressure before neutralization with aqueous ammonia (23%) and extraction with diethylether. The organic phase was dried (MgSO$_4$) and concentrated under reduced pressure to give a pink oil of the title compound (102.1 g )

A solution of the title alkene compound II (50.0 g, 0.11 mol) in methanol was added to a stirred solution of anhydrous HCl in methanol (200 mL). After stirring at room temperature for 30 minutes the solvent was removed under

2,2-Dimethyl-propionic Acid 5-Cyano-2-[4-dimethylamino-1-(4-fluoro-phenyl)-but-1-enyl]-benzyl Ester, Hydrogen Sulfate Method 4C. A solution of pivaloyl chloride (29 g, 0.24 mol) was added to a stirred solution of 4-[4-Dimethylamino-1-(4-fluoro-phenyl)-1-hydroxy-butyl ]-3-hydroxymethyl-benzonitrile (85.5 g, 0.21 mol) in acetonitrile (290 mL) at 0° C. The reaction mixture was stirred for a further 60 minutes before concentrated $H_2SO_4$ (32.5 g, 0.33 mol) was added. Once the addition was complete, the reaction was heated at 70° C. for 180 minutes. The reaction mixture was allowed to cool to room temperature, and the acetonitrile removed under reduced pressure, toluene (200 mL) was added and removed under reduced pressure to give the title compound as a pale pink oil. (112.4 g).

2,2-Dimethyl-propionic Acid 5-Cyano-2-[4-dimethylamino-1-(4-fluoro-phenyl)-but-1-enyl]-benzyl Ester, Hydrogen Chloride Method 4D. Pivaloyl chloride (7.6 g, 0.63 mol) was added dropwise to a stirred solution of 4-[4-Dimethylamino-1-(4-fluoro-phenyl)-1-hydroxy-butyl]-3-hydroxymethyl-benzonitrile (21.35 g, 0.052 mol) in acetonitrile (21.35 g) at room temperature. Once the addition was complete, a solution of methanesulphonyl chloride (6.1 g, 0.053 mol) in $CH_2Cl_2$ (50 mL) was added, followed by the addition of triethylamine (10.6 g, 0.105 mol). The reaction mixture was stirred for a further 30 minutes, poured into water, extracted with $CH_2Cl_2$, the organic phase was dried ($MgSO_4$) and concentrated under reduced pressure. The resultant oil was then dissolved in anhydrous ethanol/HCl, concentrated under reduced pressure and treated with diethylether, filtered to give the alkene HCl salt (22.6 g, 98%).

Example 5

2,2-Dimethyl-propionic Acid 5-Cyano-2-[1-(4-fluoro-phenyl)-methanoyl]-benzyl Ester.

Method 5A. To a stirred solution of the HCl salt of the alkene 2,2-dimethyl-propionic acid 5-cyano-2-[4-dimethylamino-1-(4-fluoro-phenyl)-but-1-enyl ]-benzyl ester (165 g, 0.337 mol) in $H_2O$ (1100 mL) was added a solution of $NaMnO_4$ in $H_2O$ (40% vv) (3.7 mol) at such a rate that the reaction temperature was maintained between 45–50° C. Once the addition was complete, the reaction mixture was allowed to cool to room temperature and filtered. The solid filtrate was washed with cold water (3×150 mL), and the solid residue was stirred in acetone (2000 mL) and filtered, evaporation gave the crude ketone which was purified by filtration through a silica plug (eluent hexane: ethyl acetate 8:2) to give the title ketone as a pure compound 82 g, (75%). MP=81° C. $^1H$ NMR (DMSO-$D_6$): 0.9 (s, 9H), 5.1 (s, 2H), 7.35–7.5 (m, 3H), 7.65 (d, J=7 Hz 1H), 7.8–7.9 (m, 2H), 8.0 (m, 1H), 8.1 (s, 1H).

$^{13}C$; NMR (DMSO-D6): 26.5, 63.01, 113.183, 116.0, 116.36, 118.02, 129.35, 132.19, 132.58, 133.03, 133.18, 133.34, 135.98, 141.7, 163.62, 167.65, 176.87, 193.94 Anal. Calcd for $C_{20}H_{18}NO_3F$: C, 70.79; H, 5.35; N, 4.13. Found, C, 70.49; H, 5.30; N, 4.07.

2,2-Dimethyl-propionic Acid 5-Cyano-2-[1-(4fluoro-phenyl)-methanoyl]-benzyl Ester.

Method 5B. Ozone in $O_2$ was bubbled through a stirred solution of the alkene 2,2-dimethyl-propionic acid 5-cyano-2-[4-dimethylamino-1-(4-fluoro-phenyl)-but-1-enyl]-benzyl ester (38.0 g, 0.093 mol) in $H_2O$ (1300 mL) and concentrated HCl (70 ml), with the reaction followed by HPLC. During the reaction, a white precipitate formed, and at the end of the reaction the white solid was filtered, washed with water and dried under reduced pressure to give the protected title ketone as a pure compound (22.5 g, 72%).

2,2-Dimethyl-propionic Acid 5-Cyano-2-[]-(4-fluoro-phenyl)-methanoyl]-benzyl Ester.

Method 5C. To a suspension the alkene 2,2-dimethyl-propionic acid 5-cyano-2-[4-dimethylamino-1-(4-fluoro-phenyl)-but-1-enyl]-benzyl ester, $H_2SO_4$ (11.0 g, 0,022 mole) in water (250 ml) and ethyl acetate (100 ml) was added $NaIO_4$ (30 g, 0.14 mole) and $RuCl_3$, hydrate (0.35 g). The suspension was stirred vigorous for 16 hours at ambient temperature. The resulting suspension was filtered through a plug of silica. The organic phase was separated and washed with water (50 ml). Evaporation of the solvent in vacuo gave the title compound as an oil which crystallised on standing. Yield: 7.4 g (99%).

Example 6

2,2-Dimethyl-propionic Acid 5-Cyano-2-[1-(4-fluoro-phenyl)-methanoyl]-benzyl Ester.

A solution of 4-fluorophenylmagnesium bromide, prepared from 4-fluorobromobenzene (19.2 g, 0.11 mol) and magnesium turnings (3.2 g, 0.13 mol) in dry THF (100 mL), was added dropwise to a suspension of 5-cyanophthalid (15.9 g, 0.1 mol) in dry THF (150 mL). The temperature was kept below 5° C. After the addition was complete, the reaction mixture was stirred overnight at room temperature.

Pivaloylchloride (13.3 g, 0.11 mol) was added to the reaction mixture and the temperature was raised to 60° C. for 2 hours. The resulting solution was added to a saturated solution of $NH_4Cl$ (100 mL, aq) and ice (50 g). Diethylether (100 mL) was added and the phases were separated. The organic phase was washed with 0.1 N NaOH (2×100 mL) and water (100 mL) and the organic phase was dried with $MgSO_4$ (20g). Evaporation of the solvents gave a crude title compound (29.8 g, 88%) as an oil which was deemed sufficiently pure for further reaction.

A pure sample is obtained by crystallisation from EtOAc/n-Heptane (1:9). The title compound is obtained as off white crystals.

Example 7

1-(3-Dimethylamino-propyl)-1-(4-fluoro-phenyl)-1,3-dihydro-isobenzofuran-5-carbonitrile, and its Oxalate Salt To a solution of 2,2-diznethyl-propionic acid 5-cyano-2-[1-(4-fluoro-phenyl)-methanoyl]-benzyl ester (28.5 g, 0.084 mol) in anhydrous THF (150 mL) at 0° C. was added a solution of 3-(N,N-dimethylamino)propyl magnesium chloride (2.2 equivalents) and the reaction followed by HPLC. After 1 hour at 0° C., saturated ammonium chloride was added, and the mixture was extracted with ethyl acetate, dried ($Na_2SO_4$) and concentrated under reduced pressure to give the title compound as an oil. (28.0 g, (purity 87% HPLC)). The oxalate salt is obtained by crystallisation from acetone.

Example 8

4-[1-(4-Fluoro-phenyl)-methanoyl]-3-hydroxymethyl-benzonitrile

The ketone 2,2-dimethyl-propionic acid 5-cyano-2-[1-(4-fluoro-phenyl)-methanoyl]-benzyl ester (20 g, 0.061 mol) was added to freshly prepared Na methoxide (Sodium 0.25 g, in Methanol 100 mL) and stirred at room temperature (HPLC indicated complete deprotection). The methanol was then removed under reduced pressure, dissolved in MTBE, washed with saturated ammonium chloride and dried ($MgSO_4$), and concentrated under reduced pressure to give the deprotected ketone of the title compound (14.6 g).

Example 9

4-[4-Dimethylamino-1-(4-fluorophenyl)-1-hydroxy-butyl]-3-hydroxymethyl-benzonitrile To a solution of the ketone 4-[1-(4-fluoro-phenyl)-methanoyl]-3-hydroxymethyl-benzonitrile (15.0 g, 0.046 mol) in anhydrous THF at 0° C. was added a solution of 3-(N,N-dimethylamino)propyl magnesium chloride (2.2 equivalents) and the reaction followed by HPLC. After I hour at 0° C., saturated ammonium chloride was added, and the mixture was extracted with MTBE, dried ($MgSO_4$) and concentrated under reduced pressure to give the title compound as an oil. (16.7 g (purity 85%)).

What is claimed is:

1. A method for the preparation of citalopram comprising reaction of a compound of Formula IV

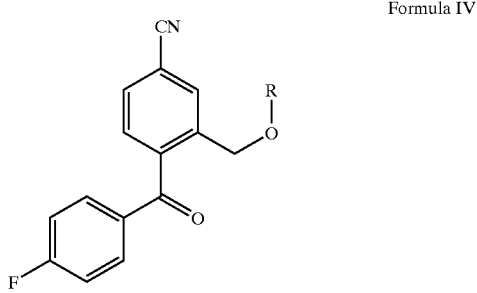

Formula IV wherein R is $C_{1-6}$ alkyl, acyl, $C_{1-6}$ alkylsulfonyl or arylsulfonyl, with 3-(N,N-dimethylamino)-propyl magnesium halide, to afford citalopram

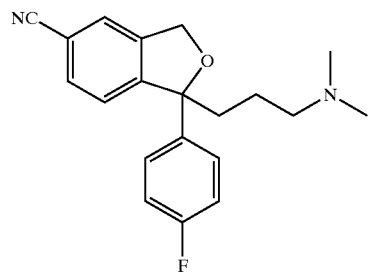

Formula I which is isolated as the base or a pharmaceutically acceptable salt thereof.

2. The method of claim 1 characterised in that the intermediate of Formula IV is prepared by oxidation of the corresponding compound of Formula V:

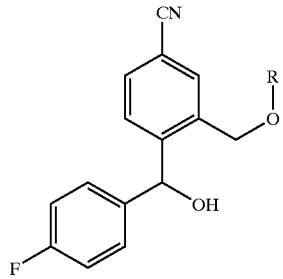

Formula V wherein R is as defined in claim 1.

3. The method of claim 2 characterised in that the compound of Formula V is prepared by protection of the hydroxymethylalcohol of (4-cyano-2-hydroxymethylphenyl) (4-fluorophenyl)methanol of Formula VI:

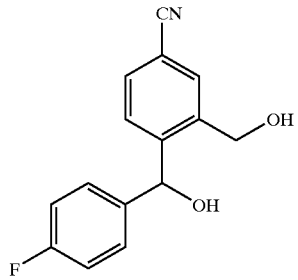

Formula VI

4. The method of claim 1 characterised in that the intermediate of Formula IV is prepared by oxidative cleavage of the corresponding compound of Formula VII:

Formula VII

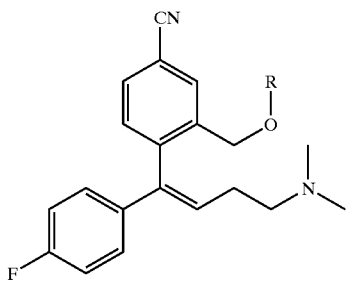

wherein R is as defined in claim 1.

5. The method of claim 4 characterised in that the oxidative cleavage of the compound of Formula VII is effected by oxidation.

6. The method of claim 4 characterised in that the intermediate alkene of Formula VII is prepared by protection and dehydration of the corresponding compound of Formula III:

Formula III

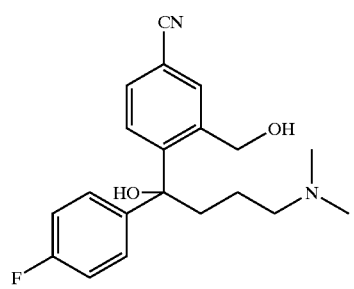

wherein the compound of Formula III is the R-enantiomer.

7. The method of claim 1 characterised in that the intermediate of Formula IV is prepared by the reaction of 5-cyanophthalide with 4-fluorophenylmagnesiumhalide, followed by the reaction with R-X to prepare the ketone compound of Formula IV, wherein R is as defined in claim 1 and X is a leaving group.

8. The method for the preparation of the racemic compound of Formula III comprising the steps of a) deprotecting a compound of Formula IV Formula IV

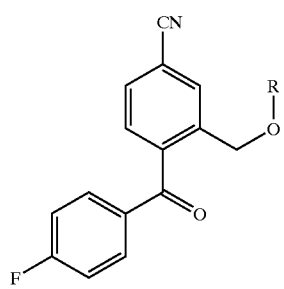

wherein R is as defined in claim 1 b) reacting the resulting compound of Formula VIII

Formula VIII

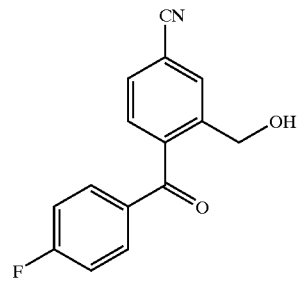

with 3-(N,N-dimethylamino)propyl magnesium halide, to prepare the racemic compound of Formula III

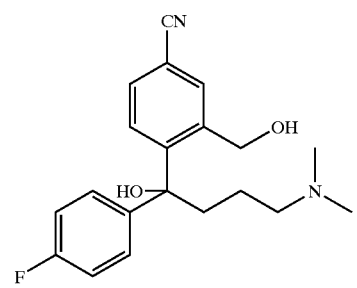

9. The method of claim 1 wherein R is acyl.

10. A compound of Formula IV:

Formula IV

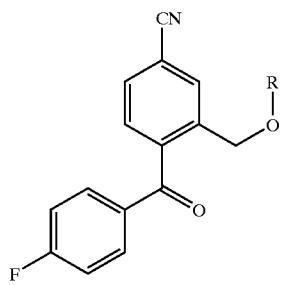

wherein R is $C_{1-6}$ alkyl, acyl, $C_{1-6}$ alkylsulfonyl or arylsulfonyl.

11. The method of claim 1, wherein the 3-N,N-dimethylamino)propyl magnesium halide is 3-(N,N-dimethylamino)propyl magnesium chloride.

12. The method of claim 4, wherein said oxidation is performed by $MnO_4^-$ (permanganates), ozone, $RuCl_3$ or $OsO_4$.

13. The method of claim 7, wherein the 4-fluorophenylmagnesium halide is 4-fluorophenylmagnesium bromide.

14. The method of claim 7, wherein R-X is selected from the group consisting of pivaloylchloride, 3,5-dimethoxybenzoylchloride, methyliodide, ethylbromide, tosylchloride, $Me_2SO_4$ or $MeSO_2Cl$.

15. The method of claim 8, wherein the 3-(N,N-dimethylamino)propyl magnesium halide is 3-(N,N-dimethylamino)propyl magnesium chloride.

16. The method of claim 9, wherein said acyl is selected from the group consisting of pivaloyl, acetyl, or optionally substituted benzoyl.

17. The compound of claim 10, wherein R is selected from the group consisting of pivaloyl, acetyl or optionally substituted benzoyl.

* * * * *